US009006280B2

(12) United States Patent
Nabeta

(10) Patent No.: US 9,006,280 B2
(45) Date of Patent: Apr. 14, 2015

(54) PYRAZOLONE DERIVATIVE FORMULATIONS

(75) Inventor: Kiichiro Nabeta, Tokyo (JP)

(73) Assignees: Teikoku Pharma USA, Inc., San Jose, CA (US); Techno Guard Co., Ltd., Kanagawa (JP)

( * ) Notice: Subject to any disclaimer, the term of this patent is extended or adjusted under 35 U.S.C. 154(b) by 328 days.

(21) Appl. No.: 12/621,271

(22) Filed: Nov. 18, 2009

(65) Prior Publication Data
US 2010/0130577 A1  May 27, 2010

Related U.S. Application Data

(60) Provisional application No. 61/116,564, filed on Nov. 20, 2008.

(51) Int. Cl.
| | |
|---|---|
| A61K 31/415 | (2006.01) |
| C07D 231/10 | (2006.01) |
| C07D 231/52 | (2006.01) |
| A61K 31/4152 | (2006.01) |
| A61K 9/00 | (2006.01) |
| A61K 47/10 | (2006.01) |
| A61K 47/12 | (2006.01) |
| A61K 47/24 | (2006.01) |
| A61K 47/26 | (2006.01) |

(52) U.S. Cl.
CPC .......... *A61K 31/4152* (2013.01); *A61K 9/0019* (2013.01); *A61K 47/10* (2013.01); *A61K 47/12* (2013.01); *A61K 47/24* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,981,730 A | 9/1976 | Takahashi et al. | |
| 4,211,836 A | 7/1980 | Yoneyama et al. | |
| 4,360,518 A | 11/1982 | Rovee et al. | |
| 4,684,632 A | 8/1987 | Schulz et al. | |
| RE35,801 E | 5/1998 | Nishi et al. | |
| 5,968,967 A | 10/1999 | Tanikawa et al. | |
| 6,653,319 B1 | 11/2003 | Xiang et al. | |
| 6,972,283 B2 | 12/2005 | Fujikura et al. | |
| 7,211,596 B2 | 5/2007 | Yoshida et al. | |
| 2002/0182248 A1* | 12/2002 | Yamauchi et al. ............ 424/450 |
| 2003/0039613 A1* | 2/2003 | Unger et al. ................ 424/9.51 |
| 2003/0138481 A1* | 7/2003 | Zadi ............................. 424/450 |
| 2003/0162775 A1 | 8/2003 | Singh et al. | |
| 2004/0162330 A1* | 8/2004 | Yoshida et al. ............... 514/404 |
| 2005/0008664 A1 | 1/2005 | Claxton et al. | |
| 2005/0276763 A1 | 12/2005 | Pfeifer et al. | |
| 2006/0189682 A1 | 8/2006 | Payne et al. | |
| 2007/0049632 A1 | 3/2007 | Banner et al. | |
| 2007/0116729 A1 | 5/2007 | Palepu | |
| 2007/0178147 A1* | 8/2007 | Desai et al. .................. 424/450 |
| 2008/0227807 A1 | 9/2008 | Hutchinson et al. | |

FOREIGN PATENT DOCUMENTS

| | | |
|---|---|---|
| CN | 1415284 | 5/2003 |
| CN | 1449754 | 10/2003 |
| CN | 1493283 | 5/2004 |
| CN | 1525856 | 9/2004 |
| CN | 1555261 | 12/2004 |
| CN | 101288650 | 10/2008 |
| EP | 1386606 | 2/2004 |
| JP | H0531523 | 5/1993 |
| JP | H0840936 | 2/1996 |
| JP | H0952831 | 2/1997 |
| JP | H11209307 | 8/1999 |
| JP | 2006-257020 | * 9/2006 |
| JP | 2008-280253 | 11/2008 |
| TW | 200519080 A | 6/2005 |
| TW | 200812567 A | 3/2008 |

OTHER PUBLICATIONS

English translation of JP 2006-257020 (2006).*
Griesser, in Chapter 8, The Importance of Solvates (pp. 211-233), in the text, Polymorphism: In the Pharmaceutical Industry, Hilfiker, 2006.*
Britain, pp. 126-127, 2008 (http://www.netlibrary.com/nlreader.dll?bookid=12783&filename=Page_126.html).*
Higashi et al, Edaravone (3-methyl-1-phenyl-2-pyrazolin-5-one), a novel free radical scavenger, for treatment of cardiovascular diseases. Rec. Pat. Cardio. Drug Disc. 2006;1:85-93.
Communication for European Patent application No. 09828170.2, Mailed on Dec. 5, 2013, 8 pages.
Third Office Action for Chinese Patent Application No. 200980135384.5, mailed on Dec. 11, 2013, 7 pages.
Office Action issued for Eurasian patent application No. 201100152, mailed Jul. 24, 2013, 3 pages.

* cited by examiner

*Primary Examiner* — Bong-Sook Baek
(74) *Attorney, Agent, or Firm* — Brian E. Davy; Bret E. Field; Bozicevic, Field & Francis, LLP

(57) ABSTRACT

Pyrazolone derivative formulations are provided. The formulations include a pyrazolone derivative active agent, e.g., edaravone, and an amphiphilic solubilizing agent. Also provided are methods of making and using the subject formulations.

10 Claims, No Drawings

PYRAZOLONE DERIVATIVE FORMULATIONS

CROSS-REFERENCE TO RELATED APPLICATIONS

Pursuant to 35 U.S.C. §119 (e), this application claims priority to the filing dates of: U.S. Provisional Patent Application Ser. No. 61/116,564 filed on Nov. 20, 2008; the disclosure of which application is herein incorporated by reference.

INTRODUCTION

3-Methyl-1-phenyl-2-pyrazolin-5-one (which is also known as edaravone) is a compound having use in a variety of different treatment applications. Some applications where edaravone has found use is in the treatment of cerebrovascular disorders such as cerebral stroke, brain tumor, cerebral ischemia observed in the acute stage of head trauma, cerebral edema and the like.

Injection formulations containing edaravone as an active ingredient have been developed. One example of an injection formulation of edaravone is an aqueous solution of edaravone containing at least one compound selected from sulfites, hydrogen sulfites and pyrosulfites, and a cysteine, where the formulation has a pH in the range of 2.5 to 6.0 (Japanese patent publication (Kokoku) No. Hei 7-121861).

Injection formulations of edaravone are challenging to prepare. Edaravone is sparingly soluble in water (2 mg/mL at 25° C.). Furthermore, edaravone exhibits less chemical stability with an increase in its concentration in an aqueous solution. In addition, edaravone is prone to decompose by oxidation in an aqueous solution. In consideration of such properties, it is difficult to stabilize edaravone as a pharmaceutical for a long period time and prepare an injection containing edaravone in an amount exceeding a saturated solubility in water.

SUMMARY

Pyrazolone derivative formulations are provided. The formulations include a pyrazolone derivative active agent, e.g., edaravone, and an amphiphilic solubilizing agent. Also provided are methods of making and using the subject formulations.

DEFINITIONS

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Alkyl" refers to monovalent saturated aliphatic hydrocarbyl groups having up to 10 carbon atoms, or up to 9 carbon atoms, up to 8 carbon atoms, or up to 3 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Cycloalkyl" refers to cyclic hydrocarbyl groups having from 3 to 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of such heterocyclic non-aromatic rings include, but are not limited to, aziridinyl, azetidinyl, piperazinyl, and piperidinyl.

"Heteroaryl" refers to a stable heterocyclic aromatic ring and fused rings containing one or more heteroatoms independently selected from N, O and S. A fused heterocyclic ring system may include carbocyclic rings and need only include one heterocyclic ring. Examples of such heterocyclic aromatic rings include, but are not limited to, pyridine, pyrimidine, and pyrazinyl.

"Aryl" refers to a monovalent aromatic hydrocarbon group derived by the removal of one hydrogen atom from a single carbon atom of a parent aromatic ring system. Typical aryl groups include, but are not limited to, groups derived from benzene, ethylbenzene, mesitylene, toluene, xylene, aniline, chlorobenzene, nitrobenzene, and the like.

"Aralkyl" or "arylalkyl" refers to an alkyl group, as defined above, substituted with one or more aryl groups, as defined above.

"Halogen" refers to fluoro, chloro, bromo and iodo. In some embodiments, the halogen is fluoro or chloro.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents. Substituents of interest include, but are not limited to: amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryl, substituted thioaryl, thioketo, thiol, alkyl-S(O)—, aryl-S(O)—, alkyl-S(O)$_2$— and aryl-S(O)$_2$—.

DETAILED DESCRIPTION

Pyrazolone derivative formulations are provided. The formulations include a pyrazolone derivative active agent, e.g., edaravone, and an amphiphilic solubilizing agent. Pyrazolone derivative formulations of interest include non-emulsion formulations. In describing a formulation as non-emulsion, "non-emulsion" refers to a composition that is not an emulsion. In an emulsion, a formulation is a liquid preparation that is a suspension of small globules of one liquid in a second liquid with which the first liquid will not mix. Also provided are methods of making and using the subject formulations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following portion sections of this specification, various aspects of formulations of interest are described first in greater detail, followed by a review of aspects of methods for preparing formulations according to embodiments of the invention, and a discussion of various illustrative applications in which the subject formulations find use.

Formulations

Aspects of the invention include storage-stable formulations of a pyrazolone derivative. By "storage-stable" is meant that the compositions may be stored for extended periods of time without significant phase separation and/or significant reduction in activity of the pyrazolone active agent. In certain embodiments, the subject compositions are stable for 2 months or longer, such as 4 months or longer, including 6 months or longer, e.g., for 1 year or longer, 1.5 years or longer, etc., when maintained at 25° C. By the phrase "without substantially decreasing the activity of the pyrazolone derivative active agent" is meant that at the end of the storage period, there is less than about 10% reduction in activity of the pyrazolone derivative active agent compared to the beginning of the storage period. In certain embodiments, the formulations exhibit substantially no (if any) color change over an extended period of time when maintained at 25° C., where by "extended period of time" is meant 2 months or longer, such as 4 months or longer, including 6 months or longer, e.g., at 1 year or longer, 1.5 years or longer, etc.

In certain embodiments, the formulations of the invention are alcohol-free. By alcohol-free is meant that the compositions include little, if any alcohol. As such, if present, alcohol is present in an amount of 3% or less, such as 2% or less, including 1% or less, including 0.5% less v/v of the composition. In some instances, the amount of alcohol is 0% v/v. As such, the formulations may not include an amount of an alcohol, e.g., ethanol. In certain embodiments, the formulations are reductant free, e.g., they are sulfite free. By reductant-free is meant that the compositions include little, if any reductant. As such, if present, a reductant is present in an amount of 3% or less, such as 2% or less, including 1% or less, including 0.5% less v/v of the composition. In some instances, the amount of reductantl is 0% v/v. In certain embodiments, the formulations are free of a stabilizer, such as a chelating agent, e.g., ethylenediamine, calcium disodium edetate or disodium edetate. By stabilizer-free is meant that the compositions include little, if any stabilizer. As such, if present, stabilizer is present in an amount of 3% or less, such as 2% or less, including 1% or less, including 0.5% less v/v of the composition. In some instances, the amount of stabilizer is 0% v/v.

Pyrazolone Derivative

As summarized above, formulations of the invention include a pyrazolone derivative active agent, which active agent may be a pyrazolone derivate, e.g., as specified below, or a physiologically acceptable salt thereof, or hydrate thereof. Of interest are pyrazolone derivatives of the following formula (I)

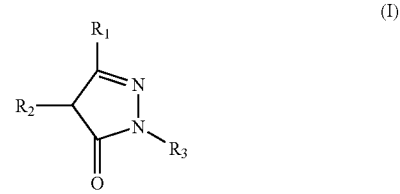

wherein:

$R_1$ represents a hydrogen atom, an aryl, an alkyl having 1 to 5 carbon atoms or an alkoxycarbonylalkyl having 3 to 6 carbon atoms in total; $R_2$ represents a hydrogen atom, an aryloxy, an arylmercapto, an alkyl having 1 to 5 carbon atoms or a hydroxyalkyl having 1 to 3 carbon atoms; or $R_1$ and $R_2$ are coupled together to form an alkylene having 3 to 5 carbon atoms; and $R_3$ is a hydrogen atom, an alkyl having 1 to 5 carbon atoms, a cycloalkyl having 5 to 7 carbon atoms, a hydroxyalkyl having 1 to 3 carbon atoms, benzyl, a naphthyl or phenyl, or a phenyl substituted by 1 to 3 substituents, which may be the same or different and selected from the group consisting of an alkoxy having 1 to 5 carbon atoms, a hydroxyalkyl having 1 to 3 carbon atoms, an alkoxycarbonyl having 2 to 5 carbon atoms in total, an alkylmercapto having 1 to 3 carbon atoms, an alkylamino having 1 to 4 carbon atoms, a dialkylamino having 2 to 8 carbon atoms in total, a halogen atom, trifluoromethyl, carboxyl, cyano, hydroxyl group, nitro, amino and acetamido)

In addition compounds described above, also of interest are physiologically acceptable salts, hydrates or solvates thereof.

In certain embodiments, the pyrazolone derivative is 3-Methyl-1-phenyl-2-pyrazolin-5-one (non-proprietary name: "Edaravone", trade name: "Radicut"; manufactured and sold by Mitsubishi Pharma Corporation, hereinafter referred to as edaravone) which is also called 3-methyl-1-phenyl-5-pyrazolone. This particular pyrazolone derivative has the structure (II):

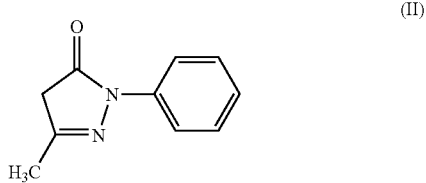

The pyrazolone active agent may be present as the pyrazolone compound, a physiologically acceptable salt thereof, or a hydrate thereof or a solvate thereof.

Embodiments of the subject formulations are characterized by having high concentrations of active agent. In certain embodiments, the pyrazolone active agent in the composition is 1.0 mg/ml or higher, including 1.5 mg/ml or higher, and in certain embodiments ranges from 1.0 to 30 mg/ml, such as 1.5 to 15 mg/ml, including 1.5 to 6.0 mg/ml. In certain embodiments, the pyrazolone active agent in the composition ranges from 1.0 to 3.5 mg/ml, including 1.5 to 3.0 mg/ml.

Amphiphilic Solubilizing Agent

Also present in the subject formulations is an amphiphilic solubilizing agent. As used herein, "solubilizing agent" refers to an agent that is capable of fully or partially dissolving or solubilizing a pyrazolone derivative active agent, e.g. edaravone. The term "amphiphilic" refers to molecules which comprise a hydrophobic tail and a polar head, as well as molecules which comprise multiple nonpolar segments and multiple polar segments.

In one case, molecules of amphiphilic compounds can have a hydrophobic tail and a polar head. The hydrophobic tail may be a hydrocarbon moiety. In one embodiment, the hydrophobic tail is a hydrocarbon chain of the form $CH_3(CH_2)_n$, with $n>1$, such as 1 to 30, including 1 to 20. The polar head may be categorized as follows: 1) anionic charged groups, e.g. carboxylates ($—CO_2^-$), sulfates ($—SO_4^-$), sulfonates ($—SO_3^-$), phosphates ($—PO_4^-$); 2) cationic charged groups, e.g., amines ($—NH_3^+$); and 3) polar uncharged groups, e.g. alcohols with hydrophobic tail is a long chain of the form $CH_3(CH_2)_n$, with $n>1$, 2, 3, or 4.

In other cases, molecules of amphiphilic compounds can have multiple hydrophobic (usually of hydrocarbon nature) and multiple hydrophilic (represented by either ionic or uncharged polar functional groups) structural regions.

Solubilizing agents to be used for the present invention include any type of solubilizing agent that has been used for pharmaceutical formulations, including, phospholipid, nonionic surfactant, or a mixture of such agents. Refined phospholipids, such as egg-yolk lecithin and soybean lecithin are employed in certain embodiments. Refined phospholipids may also include phosphatidylinocytol, phosphatidyl ethanolamine, phosphatidylserine, sphingomyeline, and phosphatidylcholine. Nonionic surfactants of interest include, but are not limited to, polyethylene glycol, polyoxyalkylene copolymer, and sorbitan fatty acid ester. One or a combination of more than one of these solubilizing agents can be used. In certain embodiments, a refined solubilizing agent is employed. In certain embodiments, a refined phospholipid is employed. In certain embodiments, egg-yolk lecithin or soybean lecithin is employed. In certain embodiments, phosphatidylcholine is employed. The amount of solubilizing agent may vary, ranging in certain embodiments from 0.01 to 100 mg/ml, such as 0.1 to 50 mg/ml.

Other Components

The subject compositions can include water in an amount that ranges, in certain embodiments, from about 70% to about 99%, such as from about 80% to about 95% v/v. The water may be any convenient water, including de-ionized water, water for injection (WFI), etc.

In certain embodiments, a pH adjusting agent is also present. pH adjusting agents of interest include, but are not limited to: sodium hydrochloride, hydrochloric acid, phosphoric acid buffer solution, and citric acid buffer solution. The pH of the formulation of the present invention can be adjusted to 5.0 to 7.5 by using the pH adjusting agent.

Certain embodiments of the formulations also include one or more solubilizing agent enhancers. As used herein, "solubilizing agent enhancer" means a component that enhances the effectiveness of the solubilizing agent. Any type of fatty acid that has been used for pharmaceutical formulations can be used as a solubilizing agent enhancer. Of interest are fatty acids with the carbon number of from 6 to 22, either natural or synthetic, and either saturated fatty acid or unsaturated fatty acid can be used, including but not limited to stearic acid, oleic acid, linoleic acid, palmitic acid, linolenic acid, and myristic acid. Refined fatty acids, e.g., oleic acid, are employed in certain embodiments. In certain embodiments, the amount of solubilizing agent enhancer ranges from 0.002 to 5 mg/ml, such as from 0.02 to 3 mg/ml.

Other additives that may be present in the formulation, as desired (e.g., stabilizing agents), include but are not limited to: glycerin, propylene glycol, polyethylene glycol (especially the average molecular weight of 400), sugars, such as D-glucose, maltose, sorbitol, mannitol, sucrose, and trehalose. The additives can act as stabilizing agents or cryoprotectant agents. A stabilizing agent or cryoprotectant agent can lower the freezing point of a solution. At a lower freezing point, the materials in the solution can be stored at longer time without decomposition.

Preparation Methods

The formulations of the invention can be prepared using any convenient protocol. In one embodiment, an injection solvent, e.g., WFI, is added to a mixture of a pyrazolone derivative and an amphiphilic solubilizing agent and roughly mixed. For rough mixing, any convenient protocol/device may be employed, such as a Homomixer (Mizuho Industrial Co., Ltd.) or High Flex Disperser (SMT), e.g., operated according to manufacturer's specifications. After the mixture is roughly mixed, it is then finely mixed, e.g., by using a high pressure emulsification machine. For fine mixing, a high pressure homogenizer such as Gaulin Homogenizer (APV-SMT) and Microfluidizer (Microfluidics) can be used. In case of using a high pressure homogenizer, the mixture may be run through any convenient number of times, such as from 2 to 50 times, including from 5 to 20 times, with a pressure that provides for the desired product, e.g., a pressure of approximately 500 to 850 kg/cm$^2$. The procedure of mixing can be carried out at a room temperature or at the temperature lower than the room temperature. In certain embodiments, the above preparation is made with nitrogen gas.

Methods of Use

The subject formulations find use in parenteral administration, e.g., via injection, of a pyrazolone derivative, e.g., edaravone, to a subject. By "parenteral administration" is meant delivery by a protocol that delivers a quantity of the subject formulations to a patient by a route other than the digestive tract, e.g., via a pulmonary route, via intramuscular injection, via intravenous delivery, etc. In certain embodiments, parenteral administration is by injection using an injection delivery device.

In certain embodiments, methods of the invention include a diagnostic step. Individuals may be diagnosed as being in need of the subject methods using any convenient protocol, and are generally known to be in need of the subject methods, e.g., they are suffering from a target disease condition or have been determined to be at risk for suffering from a target disease condition, prior to practicing the subject methods.

Utility

Formulations and methods of the invention find use in a variety of applications. Formulation and methods of invention find use in any application where a subject would benefit from being administered a pyrazolone derivative active agent, such as edaravone. In certain embodiments, the subject methods and formulations are employed in treating conditions where antioxidant activity is desired, e.g., via enhanced prostacyclin production, inhibition of lypoxygenase metabolism of arachidonic acid, inhibition of alloxan-induced lipid peroxidation, and quenching of active oxygen. General types of applications of interest include, but are not limited to the treatment of myocardial and vascular injury following ischemia and reperfusion in patients with acute myocardial infarction, atherosclerosis and chronic phase. Specific applications of interest include the treatment of cerebrovascular disorders (e.g., cerebral stroke, brain tumor, cerebral ischemia observed in the acute stage of head trauma, cerebral edema, etc.); amyotrophic lateral sclerosis, mitochondrial myopathy, etc.

By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g., terminated, such that the host no longer suffers from the condition, or at least the symptoms that characterize the condition.

Particular applications in which the subject methods and compositions find use include those described in U.S. Pat. No. 7,211,596; the disclosure of which is herein incorporated by reference in its entirety. See also Higashi et al., "Edaravone (3-Methyl-1-Phenyl-2-Pyrazolin-5-one), A Novel Free Radical Scavenger, for Treatment of Cardiovascular Diseases," Recent patents on Cardiovascular Drug Discovery (2006) 1:85-93, the disclosure of which is herein incorporated by reference in its entirety.

Kits

Also provided are kits that find use in practicing the subject methods, as described above. For example, kits for practicing the subject methods may a quantity of the composition, present in unit dosages, e.g., ampoules, or a multi-dosage format. As such, in certain embodiments the kits may one or more unit dosages (e.g., ampoules) of the formulation. In yet other embodiments, the kits may include a single multi dosage amount of the formulation.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

A. Formulation Preparation

Refined egg-yolk lecithin and oleic acid are stirred together with nitrogen gas at 40° C. Edaravone is added to the mixture and is stirred altogether with nitrogen gas at 40° C. Propylene glycol, mannitol, and distilled water for injection that is combined in advance are added to the mixture and are roughly mixed with High Flex Disperser (11,300 rpm×15 min) with nitrogen gas at 40° C. The distilled water is added to the mixture to volume. After a proper amount of sodium hydroxide is added to the mixture and the pH is adjusted to fall within the neutral range of 6.0 to 6.5, it is further mixed with a high pressure homogenizer (800 kg/cm$^2$). The mixture is filtered through a membrane filter (pore size 0.45 μm). The filtered mixture is poured in a 5 ml ampoule and the ampoule is sealed with nitrogen added to it. The ampoule is sterilized under the condition of 121° C. for 10 minutes to be used as a sample.

Samples 1 and 2 can be prepared according to the amounts listed in Table 1.

TABLE 1

| Composition | Sample 1 | Sample 2 |
| --- | --- | --- |
| Edaravone | 1.5 mg/ml | 3.0 mg/ml |
| Refined egg yolk lecithin | 18 mg/ml | 18 mg/ml |
| Oleic acid | 2.4 mg/ml | 2.4 mg/ml |
| Propylene glycol | 22.1 mg/ml | 22.1 mg/ml |
| Mannitol/sorbitol | 100 mg/ml | 100 mg/ml |
| Distilled water | Solvent measured to volume | Solvent measured to volume |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A non-emulsion aqueous formulation comprising a pyrazolone derivative active agent, an amphiphilic solubilizing agent, a solubilizing agent enhancer, and a stabilizing agent,
   wherein said pyrazolone derivative active agent is edaravone or a pharmaceutically acceptable salt thereof;
   said solubilizing agent is a phospholipid selected from the group consisting of egg-yolk lecithin, soybean lecithin, phosphatidylinositol, phosphatidyl ethanolamine, phosphatidylserine, sphingomyelin, and phosphatidylcholine;
   said solubilizing agent enhancer is a fatty acid; and
   said stabilizing agent is selected from the group consisting of propylene glycol, sorbitol, mannitol, and combination thereof,
   wherein the non-emulsion formulation comprises 0% v/v ethanol,
   wherein said non-emulsion aqueous formulation is an injection formulation configured for parenteral administration.

2. The formulation according to claim 1, wherein said formulation has a pH ranging from 5.0 to 7.5.

3. The formulation according to claim 1, wherein said formulation is alcohol-free.

4. The formulation according to claim 1, wherein said formulation is reductant-free.

5. The formulation according to claim 1, wherein said formulation is chelator-free.

6. The formulation according to claim 1, wherein said pyrazolone derivative active agent is present in an amount ranging from 1.0 to 30 mg/ml.

7. The formulation according to claim 1, wherein said pyrazolone derivative active agent is present in an amount ranging from 1.5 to 3.0 mg/ml.

8. A method comprising parenterally administering to a subject the non-emulsion aqueous formulation according to claim 1.

9. A kit comprising a unit dosage of the non-emulsion aqueous formulation according to claim 1.

10. The formulation according to claim 1, wherein said formulation is configured for intravenous administration.

* * * * *

UNITED STATES PATENT AND TRADEMARK OFFICE
CERTIFICATE OF CORRECTION

| | | |
|---|---|---|
| PATENT NO. | : 9,006,280 B2 | Page 1 of 1 |
| APPLICATION NO. | : 12/621271 | |
| DATED | : April 14, 2015 | |
| INVENTOR(S) | : Nabeta | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 707 days.

Signed and Sealed this
Twentieth Day of October, 2015

Michelle K. Lee
*Director of the United States Patent and Trademark Office*